(12) United States Patent  
Lee et al.

(10) Patent No.: US 9,309,371 B2
(45) Date of Patent: Apr. 12, 2016

(54) POLYMERIZATION INITIATOR, MODIFIED-CONJUGATED DIENE POLYMER AND TIRE PRODUCED THEREFROM

(71) Applicant: LG CHEM, LTD., Seoul (KR)

(72) Inventors: Ro Mi Lee, Daejeon (KR); Du Weon Yoon, Daejeon (KR); Chang Woo Kim, Daejeon (KR); Jun Hyun Park, Daejeon (KR); Sang Mi Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/096,800

(22) Filed: Dec. 4, 2013

(65) Prior Publication Data

US 2014/0163163 A1 Jun. 12, 2014

(30) Foreign Application Priority Data

Dec. 6, 2012 (KR) .......................... 10-2012-0140701

(51) Int. Cl.
*C08F 36/06* (2006.01)
*C08L 47/00* (2006.01)
*C07D 213/16* (2006.01)
*C08K 3/36* (2006.01)
*C08F 2/00* (2006.01)
*C08F 4/48* (2006.01)
*C08F 236/10* (2006.01)
*C08L 9/02* (2006.01)

(52) U.S. Cl.
CPC ................. *C08K 3/36* (2013.01); *C07D 213/16* (2013.01); *C08F 2/00* (2013.01); *C08F 4/48* (2013.01); *C08F 36/06* (2013.01); *C08F 236/10* (2013.01); *C08L 9/02* (2013.01); *C08L 47/00* (2013.01); *Y02T 10/862* (2013.01)

(58) Field of Classification Search
CPC ........ C08F 36/06; C08L 47/00; C07D 213/16
See application file for complete search history.

(56) References Cited

U.S. PATENT DOCUMENTS

2009/0203861 A1    8/2009  Lee

FOREIGN PATENT DOCUMENTS

| JP | 5035835 B2 | 7/2012 |
| KR | 10-2009-0114478 A | 11/2009 |
| KR | 10-2011-0052523 A | 5/2011 |
| KR | 10-2011-0120622 | * 11/2011 |
| KR | 10-2011-0120622 A | 11/2011 |

* cited by examiner

*Primary Examiner* — Robert Harlan
(74) *Attorney, Agent, or Firm* — Dentons US LLP

(57) ABSTRACT

The present disclosure relates to a polymerization initiator and a modified conjugated diene polymer prepared using the same, and more particularly to a polymerization initiator which is a compound represented by the following formula 1, and a modified conjugated diene polymer prepared using the same:

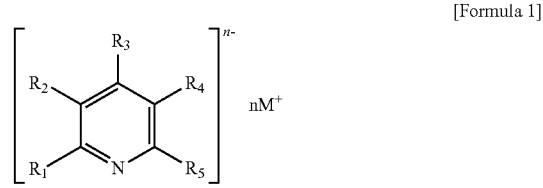

[Formula 1]

wherein $R_1$ to $R_5$ are each independently hydrogen or a $C_{1-10}$ alkylgroup or its carbanion; n– represents the number of negative charges of the carbanion and is 1– to 5–; M is a metal; and n is equal to the number of carbanions in $R_1$ to $R_5$.

8 Claims, No Drawings

POLYMERIZATION INITIATOR, MODIFIED-CONJUGATED DIENE POLYMER AND TIRE PRODUCED THEREFROM

The present invention claims the benefit of Korean Patent Application No. 10-2012-0140701, filed on Dec. 6, 2012, which is hereby incorporated by reference for all purposes as if fully set forth herein.

BACKGROUND OF THE INVENTION

1. Field of the Invention

The present disclosure relates to a polymerization initiator, a modified conjugated diene polymer and a tire produced therefrom.

2. Description of the Prior Art

At present, conjugated diene polymers having low rolling resistance and excellent wear resistance and wet skid resistance are used as rubber for tires.

The rolling resistance of tires is reduced by reducing the hysteresis loss of vulcanized rubber. As rubber materials having a low hysteresis loss, natural rubber and the like are known, but they have a problem of low wet skid resistance.

For this reason, conjugated diene polymers such as styrene-butadiene rubber (hereinafter referred to as SBR) or butadiene rubber (hereinafter referred to as BR), which are prepared by emulsion polymerization or solution polymerization, have recently been used as rubber for tires.

Meanwhile, solution-polymerized SBR is prepared using an anionic polymerization initiator. As the anionic polymerization initiator, alkyl lithium is mainly used.

However, the above rubber materials for tires still have problems in that improvement in the hysteresis loss or wear resistance thereof is insufficient and blending of the rubber materials does not show sufficient effects and reduces the processability of the rubber materials.

SUMMARY OF THE INVENTION

It is an object of the present disclosure to solve the above-described problems occurring in the art and to provide an end-modified conjugated diene polymer, which has a high vinyl content, excellent compatibility with inorganic fillers and good properties in terms of braking force, viscoelasticity, wear performance and fuel economy, and a tire comprising the end-modified conjugated diene polymer and having low rolling resistance and excellent wet skin resistance.

Another object of the present disclosure is to provide a polymerization initiator for use in the preparation of the end-modified conjugated diene polymer, a solution thereof and a composition thereof.

To achieve the above objects, the present disclosure provides a polymerization initiator, a compound represented by the following formula 1:

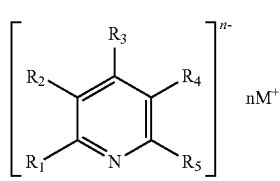

Formula 1 wherein $R_1$ to $R_5$ are each independently hydrogen or a $C_{1-10}$ alkylgroup or its carbanion; n− represents the number of negative charges of the carbanion and is 1− to 5−; M is a metal; and n is equal to the number of carbanions in $R_1$ to $R_5$.

The present disclosure also provides a polymerization initiator solution comprising one or more compounds represented by formula 1, an aprotic solvent and a polar solvent.

The present disclosure also provides a polymerization initiator composition comprising two or more compounds represented by the following formula 2.

The present disclosure also provides a modified conjugated diene polymer comprising a group represented by the following formula 2:

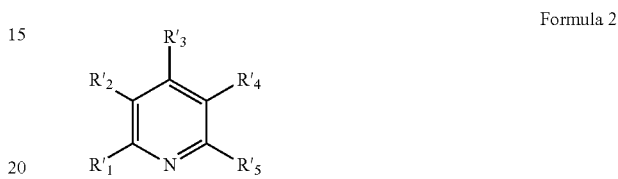

Formula 2 wherein $R'_1$, to $R'_5$ are each independently hydrogen or a $C_{1-10}$ alkyl or alkylenegroup, and at least in $R'_1$, to $R'_5$ is an alkylenegroup linked to the conjugated diene polymer chain.

The present disclosure also provides a modified conjugated diene polymer composition comprising 100 parts by weight of the modified conjugated diene polymer and 10-200 parts by weight of an organic filler.

The present disclosure also provides a tire produced from the modified conjugated diene polymer composition.

DETAILED DESCRIPTION OF THE INVENTION

Hereinafter, description will be made in detail on a polymerization initiator, a solution thereof, a composition thereof, a polymer prepared therefrom, a composition comprising the same and a tire produced therefrom.

A polymerization initiator according to the present disclosure is a compound represented by the following formula 1:

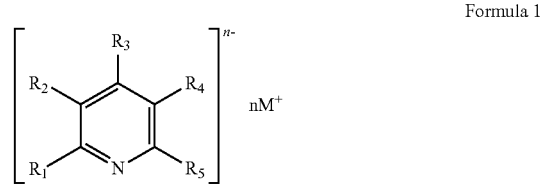

Formula 1 wherein $R_1$ to $R_5$ are each independently hydrogen or a $C_{1-10}$ alkylgroup or its carbanion; n− represents the number of negative charges of the carbanion and is 1− to 5−; M is a metal; and n is equal to the number of carbanions in $R_1$ to $R_5$.

In one embodiment of the present disclosure, $R_1$ to $R_5$ are each independently hydrogen or $C_{1-5}$ alkylgroup or its carbanion. In another embodiment, $R_1$ to $R_5$ are each independently hydrogen or $C_{1-2}$ alkylgroup or its carbanion.

In one embodiment, n− is 1− to 3−. In another embodiment, n− is 1− or 2−.

In one embodiment, M is Li, Na, K or Cs. In another embodiment, M is Li or Na.

The polymerization initiator according to the present disclosure is highly active and ensures sufficient randominization of monomers to produce a high-vinyl conjugated diene polymer having a decreased content of block styrene.

In one embodiment, a method for preparing the polymerization initiator of the present disclosure comprises reacting a compound represented by the following formula 3 with a compound represented by the following formula 4:

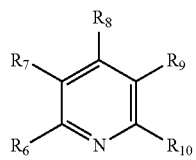

Formula 3 wherein $R_6$ to $R_{10}$ are each independently hydrogen or a $C_{1-10}$ alkylgroup; and $$R(Li)_x \quad \text{Formula 4}$$

wherein R is a $C_{1-20}$ hydrocarbylgroup, and x is an integer ranging from 1 to 4.

In one embodiment, $R_6$ to $R_{10}$ are each independently hydrogen or a $C_{1-10}$ alkylgroup. In another embodiment, $R_6$ to $R_{10}$ are each independently hydrogen or a $C_{1-5}$ alkylgroup. In still another embodiment, $R_6$ to $R_{10}$ are each independently hydrogen or a $C_{1-2}$ alkylgroup.

In still another embodiment, at least one of $R_6$ to $R_{10}$ is a $C_{1-10}$ alkylgroup, a $C_{1-5}$ alkylgroup, a methylgroup or an ethylgroup.

In one embodiment, the compound represented by formula 3 may be one or more selected from the group consisting of 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2,3,4-trimethylpyridine, 2,4,5-trimethylpyridine, 2,4,6-trimethylpyridine, 2,3,4,5-tetramethylpyridine, 2,3,4,6-tetramethylpyridine and 2,3,5,6-tetramethylpyridine.

In one embodiment, R in formula 4 is a $C_{2-8}$ hydrocarbylgroup, a $C_{1-20}$ alkylgroup or a $C_{2-8}$ alkylgroup.

In another embodiment, R may be an aliphatic or alicyclicgroup, for example, an alkyl, cycloalkyl, cycloalkylalkyl, alkylcycloalkyl, aryl or alkylarylgroup.

In still another embodiment, R is methyl, ethyl, n-propyl, isopropyl, n-butyl, isobutyl, t-butyl, n-amyl, isoamyl, n-hexyl, n-octyl, n-decyl, cyclopentyl, cyclohexylethyl, cyclopentylethyl, methylcyclopentylethyl, cyclopentyl, dimethylcyclopentyl, ethylcyclopentyl, methylcyclohexyl, dimethylcyclohexyl, ethylcyclohexyl or isopropylhexyl.

In one embodiment, the compound represented by formula 4 may be an organic lithium compound, for example, p-tolyl lithium, 4-phenyl lithium, 4-butylcyclohexyl lithium, 4-cyclohexylbutyl lithium, lithium dialkylamine, lithium dialkyl phosphine, lithium alkyl aryl phosphine, lithium diaryl phosphine or the like.

In another embodiment, the method for preparing the polymerization initiator of the present disclosure comprises reacting the component of formula 3 with the compound of formula 4 with stirring at a predetermined reaction temperature in the presence of a polar additive and a solvent.

In one embodiment, the method for preparing the polymerization initiator of the present disclosure may be carried out according to the following reaction scheme 1:

Reaction scheme 1

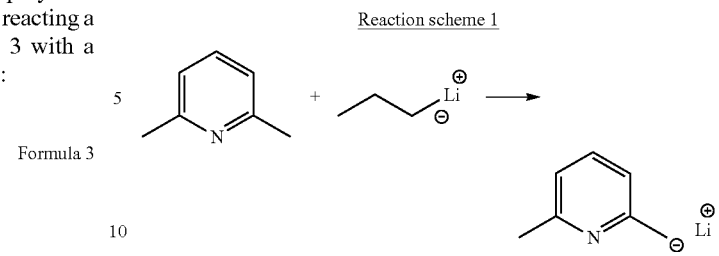

In another embodiment, the method for preparing the polymerization initiator of the present disclosure may be carried out according to the following reaction scheme 2:

Reaction scheme 2

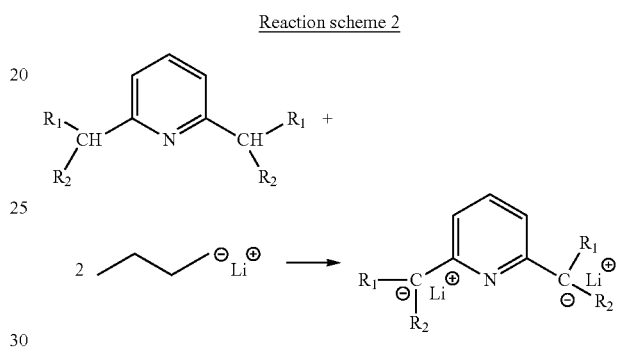

The reaction temperature may be, for example, −70 to 50° C. or 0 to 50° C. In this temperature range, the activity of the compound represented by formula 4 is not reduced, and the reaction is easily carried out.

The reaction time may be 5 minutes to 48 hours, 30 minutes to 30 hours, or 50 minutes to 26 hours. In this reaction time range, the activity of the compound represented by formula 4 is not reduced, and the reaction is easily carried out.

In one embodiment, the polar additive is a base. In another embodiment, the polar additive is ether, amine or a mixture thereof. In still another embodiment, the polar additive is selected from the group consisting of tetrahydrofuran, ditetrahydrofurylpropane, diethylether, cycloamyl ether, dipropylether, ethylene dimethyl ether, diethyleneglycol, dimethyl ether, tert-butoxyethoxyethane, bis-(2-dimethylaminoethyl) ether, (dimethylaminoethyl)ethyl ether, trimethylamine, triethylamine, tripropylamine and tetramethylethylenediamine. In another embodiment, the polar additive is triethylamine or tetramethylethylenediamine.

The solvent may be an aprotic solvent.

In one embodiment, the molar ratio between the compound of formula 3 and the compound of formula 4 is 0.01:1 to 1:0.01, 0.1:1 to 1:0.1, or 0.5:1 to 1:0.5.

In another embodiment, the molar ratio between the compound of formula 3 and the compound of formula 4 is 1:1 to 1:2, 1:1.01 to 1:1.50, or 1:1.1 to 1:1.4.

In addition, in the method for preparing the polymerization initiator of the present disclosure, a polar solvent may optionally be added to the aprotic solvent in order to increase the rate of polymerization or control the structure of the polymer. In this case, the solubility of the solute is increased to promote the reaction.

The polymerization initiator solution of the present disclosure comprises one or more compounds represented by the following formula 1, a solvent and a polar additive:

Formula 1

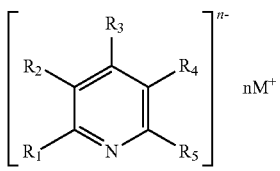

wherein $R_1$ to $R_5$ are each independently hydrogen or a $C_{1-10}$ alkylgroup or its carbanion; n– represents the number of negative charges of the carbanion and is 1– to 5–; M is a metal; and n is equal to the number of carbanions in $R_1$ to $R_5$.

In one embodiment, the one or more compounds represented by formula 1 may be a mixture of a compound wherein n is 1 with a compound wherein n is 2-5. In this case, the compound of formula 1 wherein n is 2-5 can substantially serves as a coupling agent, because the initiation of polymerization occurs in 2 to 5 directions. Thus, a high-molecular-weight polymer can be obtained, which has not only improved compatibility with an inorganic filler which is added to a rubber polymer composition for tires, but also various improved properties.

In one embodiment, the one or more compounds represented by formula 1 may be a mixture of the compound of formula 1, wherein $R_2$ to $R_4$ 1 are each hydrogen, $R_1$ is an alkylgroup, and $R_5$ is a carbaniongroup formed by removal of hydrogen cation from an alkylgroup (therefore, n is 1–), with the compound of formula 1 wherein $R_2$ to $R_4$ in formula 1 are each hydrogen, and $R_1$ and $R_5$ is a carbaniongroup formed by removal of hydrogen cation from an alkylgroup (therefore, n is 2–).

In one embodiment, the solvent is an aprotic solvent. In another embodiment, the solvent is a hydrocarbon solvent. In still another embodiment, the solvent is an aromatic hydrocarbon solvent, an alicyclic hydrocarbon solvent or an aliphatic hydrocarbon solvent. Specifically, the solvent may be one or more selected from among benzene, toluene, xylene, ethylbenzene, cyclohexane, methyl cyclohexane, cyclooctane, propane, butane, pentane, n-hexane, n-heptane, octane, decane and so on.

In one embodiment, the polar additive is a base, and in another embodiment, it may be ether, amine or a mixture thereof. The polar additive may be used in an amount of 0.1-40 moles or 0.1-10 moles per mole of the compound represented by formula 1.

When a conjugated diene monomer is copolymerized with a vinyl aromatic monomer, a block copolymer is easily prepared due to the difference in reaction rate between the monomers. However, when a polar additive is added to the monomers, it increases the reaction rate of the vinyl aromatic compound having a slow reaction rate to induce, for example, a random copolymer.

In one embodiment, the polar additive may be added during synthesis of the polymerization initiator or preparation of the conjugated diene polymer.

When the polar additive is added during preparation of the conjugated diene polymer, it may be added in an amount of, for example, about 300-1,500 parts by weight based on a total of 100 parts by weight of the monomer added.

In one embodiment, the polymerization initiator solution may be used for homopolymerization of a conjugated diene monomer or copolymerization of a conjugated diene monomer and a vinyl monomer.

The polymerization initiator composition of the present disclosure comprises two or more compounds represented by the following formula 1:

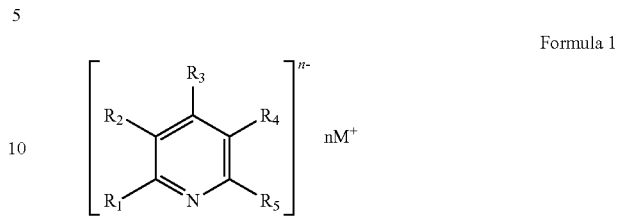

Formula 1 wherein $R_1$ to $R_5$ are each independently hydrogen or a $C_{1-10}$ alkylgroup or its carbanion; n– represents the number of negative charges of the carbanion and is 1– to 5–; M is a metal; and n is equal to the number of carbanions in $R_1$ to $R_5$.

In one embodiment, the molar ratio between the compound of formula 1 wherein n is 1 and the compound of formula 1 wherein n is 2 to 5 is 1:0.0001 to 0.0001:1, 1:0.1 to 1:2.0, or 1:0.3 to 1:1.3.

In one embodiment, the polymerization initiator composition of the present disclosure may comprise the compound of formula 1 wherein n in formula 1 is 2 and the compound of formula 1 wherein n is 2 to 5. In this case, the compound of formula 1 wherein n is 2-5 can substantially serve as a coupling agent, because the initiation of polymerization occurs in 2 to 5 directions. Thus, a high-molecular-weight polymer can be obtained, which has not only improved compatibility with an inorganic filler which is added to a rubber polymer composition for tires, but also various improved properties.

In another embodiment, the polymerization initiator composition of the present disclosure may comprises the compound of formula 1 wherein $R_2$ to $R_4$ are each hydrogen, $R_1$ is an alkylgroup, and $R_5$ is a carbaniongroup formed by removal of hydrogen cation from an alkylgroup (therefore, n is 1–), with the compound of formula 1 wherein $R_2$ to $R_4$ in formula 1 are each hydrogen, and $R_1$ and $R_5$ is a carbaniongroup formed by removal of hydrogen cation from an alkylgroup (therefore, n is 2–).

The modified conjugated diene polymer of the present disclosure comprises a group represented by the following formula 2:

Formula 2 wherein $R'_1$ to $R'_5$ are each independently hydrogen or a $C_{1-10}$ alkyl or alkylenegroup, and at least one of $R'_1$ to $R'_5$ is an alkylenegroup linked to the conjugated diene polymer chain.

In one embodiment, the conjugated diene polymer may have a vinyl content of 25% or more, 25-60%, 30-45%, or 35-45%. In this vinyl content range, the glass transition temperature of the polymer is increased, and thus when the polymer is applied to a tire, it can satisfy physical properties required for the tire, such as running resistance and braking force, and reduce fuel consumption.

As used herein, the term "vinyl content" refers to either the content of a unit having a vinylgroup or the content of a 1,2-addition (which is not a 1,4-addition) conjugated diene monomer relative to 100 wt % of conjugated diene monomers.

In one embodiment, the modified conjugated diene polymer may be a polymer comprising either a conjugated diene monomer alone or the conjugated diene monomer and an aromatic vinyl monomer in an amount of 0.0001-40 wt % based on 100 wt % of the sum of the conjugated diene monomer and the aromatic vinyl monomer.

In one embodiment, the modified conjugated diene polymer has a weight-average molecular weight of 5,000-5,000,000, 50,000-1,000,000, 100,000-600,000, or 300,000-500,000.

In one embodiment, the modified diene polymer of the present disclosure is a modified conjugated diene random polymer.

The modified conjugated diene copolymer of the present disclosure may further comprise aromatic oil. The aromatic oil is not specifically limited, as long as it can generally be used in tire rubber compositions. For example, the aromatic oil may be TDAE (treated distillate aromatic extract) oil. In this case, the aromatic oil can greatly improve the processability of a conjugated diene polymer (e.g., SBR) having a high molecular weight.

The aromatic oil may be used in an amount of 1-100 parts by weight or 10-50 parts by weight based on 100 parts by weight of the polymer. In this aromatic oil content range, the processability of the conjugated diene polymer prepared is improved and the Mooney viscosity is maintained or increased.

Meanwhile, the modified conjugated diene polymer can be prepared, for example, by solution-polymerizing a conjugated diene monomer using the polymerization initiator in the presence of an aprotic solvent.

The solution polymerization has advantages over emulsion polymerization in that the vinyl content and aromatic vinyl monomer (unit) content of the polymer, which determine the physical properties of rubber, can be optionally controlled, and the molecular weight and physical properties of the polymer can be easily controlled by coupling or modification. Thus, the modified conjugated diene polymers (e.g., SBR or BR) prepared by solution polymerization show small end-chain movement and have affinity or compatibility with carbon black, and thus are frequently used as tire rubber materials.

For example, the solution polymerization may be carried out at 20° C. to 80° C. for 1-5 hours.

In the solution polymerization, the polymerization initiator may be used in an amount of, for example, 0.01-10 mmol, 0.1-2 mmol or 0.2-1.0 mmol based on 150 g of the monomer used.

In one embodiment, the conjugated diene monomer is one or more selected from the group consisting of 1,3-butadiene, isoprene, 2,3-dimethyl-1,3-butadiene, 1,3-pentadiene, 2-methyl-3-ethyl-1,3-butadiene, 3-methyl-1,3-pentadiene, 1,3-hexadiene, 2-methyl-1,3-hexadiene, and 3-butyl-1,3-octadiene. In another embodiment, the conjugated diene monomer is 1,3-butadiene or isoprene.

In one embodiment, the aromatic vinyl monomer (compound) is one or more selected from the group consisting of styrene, α-methyl styrene, 1-vinyl naphthalene, 2-vinyl naphthalene, 1-α-methyl vinyl naphthalene, 2-α-methyl vinyl naphthalene, 4-methyl styrene, vinyl toluene, 3,5-diethyl styrene, 2-ethyl-4-benzyl styrene, 4-phenyl styrene, 4-p-tolyl styrene, and 4,5-dimethyl-1-vinyl naphthalene. Preferably, the aromatic vinyl monomer is styrene.

The modified conjugated diene polymer may have a PDI of for example, 0.5-10, 0.5-5, or 1.0-1.5.

With respect to viscoelastic properties, the modified conjugated diene polymer has a Tan δ at 0° C. of 0.6-0.75 as measured at 10 Hz by DMA after mixture of silica. In this Tan δ range, the rolling resistance and wet skid resistance of a tire produced from the polymer are greatly improved compared to those of conventional tires.

In addition, the modified conjugated diene polymer of the present disclosure may have a Tan δ at 60° C. of, for example, 0.07-0.09. In this Tan δ range, the rolling resistance (RR) of a tire produced from the polymer is greatly improved compared to those of conventional tires.

The modified conjugated diene polymer rubber composition of the present disclosure comprises 100 parts by weight of the modified conjugated diene polymer and 10-200 parts by weight of an inorganic filler.

The modified conjugated diene polymer rubber composition of the present disclosure shows improved wear resistance, high wet skid resistance and low rolling resistance, because the modified conjugated diene polymer has excellent compatibility with the inorganic filler.

The inorganic filler is not specifically limited as long as it may generally be applied to the conjugated diene polymer. For example, the inorganic filler may be silica, carbon black or a mixture thereof.

The modified conjugated diene polymer rubber composition may further comprise 1-100 parts by weight of oil.

The oil may be, for example, mineral oil or a softening agent.

The oil may be used in an amount of, for example, 10-100 parts by weight or 20-80 parts by weight based on 100 parts by weight of the conjugated diene polymer. In this oil content range, the oil promotes the expression of the physical properties of the rubber composition and suitably softens the rubber composition to increase the processability of the composition.

The tire of the present disclosure is produced from the modified conjugated diene polymer rubber composition.

Hereinafter, the present disclosure will be described with reference to examples. These examples describe the polymerization initiator solution of the present disclosure and the modified conjugated diene polymer prepared using the same. These examples are for illustrative purposes only and are not intended to limit the scope of the present disclosure. Unless otherwise specified, all percentages (%) are percentages by weight.

EXAMPLES

Example 1

1) Preparation of Polymerization Initiator

In a 250-ml round bottom flask, 1.07 g (10 mmol) of 2,6-dimethylpyridine was dissolved by addition of 44.8 ml of hexane, and 4 ml (10 mmol) of 2.5 M n-butyl lithium was added to the solution. At this time, the solution was opaque yellow in color. Then, the solution was stirred for 1 hour, thereby preparing a polymerization initiator.

2) Preparation of Modified Conjugated Diene Polymer 37 g of styrene, 113 g of 1,3-butadiene and 600 g of n-hexane were introduced into a 2-L Buchi reactor, and then heated with stirring to control the internal temperature of the reactor to 60° C. When the temperature reached 60° C., 0.28 mmol of N,N,N',N'-tetramethylethylenediamine and the above-prepared polymerization initiator (0.4 mmol based on lithium) were introduced into the reactor and adiabatically heated until the reaction became stable. After adiabatic heating, the reaction temperature was increased to 70° C., and after 60 minutes, the polymerization reaction was stopped by addition of methanol. Then, 5 ml of a solution of 0.3 wt % of the antioxidant BHT (butylated hydroxytoluene) in hexane was added thereto.

The polymerization product was added to steam-heated hot water, and the solvent was removed by stirring. Then, the remaining material was roll-dried to remove the remaining solvent and water. The results of analysis of the modified conjugated diene polymer thus prepared are shown in Table 1 below.

Example 2

1) Preparation of Polymerization Initiator

In a 250-ml round bottom flask, 1.07 g (10 mmol) of 2,6-dimethylpyridine was dissolved by addition of 1.52 ml (10 mmol) of N,N,N',N'-tetramethylethylenediamine and 43.3 ml of hexane, and 4 ml (10 mmol) of 2.5 M n-butyl lithium was added to the solution. At this time, the solution changed to clear red. Then, the solution was stirred for 1 hour, thereby preparing a polymerization initiator.

It could be seen that, when the N,N,N',N'-tetramethylethylenediamine was added, the solution was maintained in a clear state, and thus the solubility was increased and the introduction of the initiator became easy.

2) Preparation of Modified Conjugated Diene Polymer

A modified conjugated diene polymer was prepared in the same manner as Example 1, except that N,N,N',N'-tetramethylethylenediamine was not added. The results of analysis of the modified conjugated diene polymer thus prepared are shown in Table 1 below.

Example 3

1) Preparation of Polymerization Initiator

In a 250-ml round bottom flask, 0.93 g (10 mmol) of 2-methyl pyridine was dissolved by addition of 1.52 ml (10 mmol) of N,N,N',N'-tetramethylethylenediamine and 43.3 ml of hexane, and ml (10 mmol) of 2.5 M n-butyl lithium was added to the solution. At this time, the solution changed to clear red. Then, the solution was stirred for 1 hour, thereby preparing a polymerization initiator.

2) Preparation of Modified Conjugated Diene Polymer

A modified conjugated diene polymer was prepared in the same manner as Example 1, except that 0.4 mmol of N,N,N', N'-tetramethylethylenediamine was added. The results of analysis of the modified conjugated diene polymer thus prepared are shown in Table 1 below.

Comparative Example 1

A conjugated diene polymer was prepared in the same manner as Example 1, except that 0.16 ml (0.4 mmol) of 2.5 M n-butyllithium (n-BuLi)/hexane solution was used instead of the polymerization initiator of the present disclosure. The polymerization product was treated in the same manner as Example 1, and the results of analysis of the conjugated diene polymer thus prepared are shown in Table 1 below.

Comparative Example 2

A conjugated diene polymer was prepared in the same manner as Comparative Example 1, except that 0.4 mmol of N,N,N',N'-tetramethylethylenediamine was used. The polymerization product was treated in the same manner as Example 1, and the results of analysis of the conjugated diene polymer thus prepared are shown in Table 1 below.

Comparative Example 3

A conjugated diene polymer was prepared in the same manner as Comparative Example 1, except that 0.8 mmol of N,N,N',N'-tetramethylethylenediamine was used. The polymerization product was treated in the same manner as Example 1, and the results of analysis of the conjugated diene polymer thus prepared are shown in Table 1 below.

The polymers prepared in the Examples and the Comparative Examples were analyzed by NMR (nuclear magnetic resonance) using conventional methods to measure the fine structure of the conjugated diene compound, the composition ratio of the conjugated diene compound to the vinyl compound, and the random or block ratio of the conjugated diene compound and the vinyl compound.

TABLE 1

| | Polymerization initiator | | Molar ratio of polar solvent/ initiator | Conjugated diene copolymer NMR(%) | | |
|---|---|---|---|---|---|---|
| | Kind | Content (mmol) | | Styrene | Block PS | Vinyl content |
| Example 1 | Formula 1 | 0.4 | 0.7 | 23.2 | 0 | 27.4 |
| Example 2 | Formula 1 | 0.4 | 1.0 | 22.1 | 0 | 26.4 |
| Example 3 | Formula 1 | 0.4 | 2.0 | 24.1 | 0 | 40.3 |
| Comparative Example 1 | n-BuLi | 0.4 | 0.7 | 23.2 | 3.5 | 18.9 |
| Comparative Example 2 | n-BuLi | 0.4 | 1.0 | 24.2 | 2.3 | 23.2 |
| Comparative Example 3 | n-BuLi | 0.4 | 2.0 | 25.4 | 0 | 36.7 |

As can be seen from the results in Table 1 above, the vinyl contents of the modified conjugated diene polymers prepared in Examples 1 to 3 were significantly higher than those of the conjugated diene polymers prepared in Comparative Examples 1 to 3 using the conventional organic lithium initiator under the condition of the same molar ratio of polar solvent/initiator.

Example 4

1) Preparation of Polymerization Initiator

In a 250-ml round bottom flask, 0.55 g (5 mmol) of 2,6-dimethylpyridine and 1.17 g (10 mmol) of N,N,N',N'-tetramethylethylenediamine were dissolved by addition of 43.88 ml of hexane, and 4 ml (10 mmol) of 2.5M n-butyl lithium was added to the solution. At this time, the solution changed to clear red. Then, the solution was stirred for 1 hour, thereby preparing a polymerization initiator.

2) Preparation of Modified Conjugated Diene Polymer 37 g of styrene, 113 g of 1,3-butadiene and 600 g of n-hexane were introduced into a 2-L Buchi reactor, and then heated with stirring to control the internal temperature of the reactor to 60° C. When the temperature reached 60° C., the above-prepared polymerization initiator (0.4 mmol based on lithium) was introduced into the reactor and adiabatically heated until the reaction became stable. After adiabatic heating, the reaction temperature was increased to 70° C., and after 60 minutes, the polymerization reaction was stopped by addition of methanol. Then, 5 ml of a solution of 0.3 wt % of the antioxidant BHT (butylated hydroxytoluene) in hexane was added thereto.

The polymerization product was added to steam-heated hot water, and the solvent was removed by stirring. Then, the remaining material was roll-dried to remove the remaining solvent and water. The results of analysis of the modified conjugated diene polymer thus prepared are shown in Table 2 below.

Example 5

A polymerization initiator was prepared in the same manner as Example 4, except that the reaction was carried out for 4 hours and 30 minutes. Using the polymerization initiator, a modified conjugated diene polymer was prepared in the same manner as Example 4. The results of analysis of the modified conjugated diene polymer thus prepared are shown in Table 2 below.

Example 6

A polymerization initiator was prepared in the same manner as Example 4, except that the reaction was carried out for 25 hours. Using the polymerization initiator, a modified conjugated diene polymer was prepared in the same manner as Example 4. The results of analysis of the modified conjugated diene polymer thus prepared are shown in Table 2 below.

Example 7

A polymerization initiator was prepared in the same manner as Example 4, except that 0.72 g (6.6 mmol) of dimethylpyridine was used. Using the polymerization initiator, a modified conjugated diene polymer was prepared in the same manner as Example 4. The results of analysis of the modified conjugated diene polymer thus prepared are shown in Table 2 below.

Comparative Example 4

A polymerization initiator was prepared in the same manner as Example 4, except that 0.4 mmol of n-butyllithium was used. Using the polymerization initiator, a modified conjugated diene polymer was prepared in the same manner as Example 4. The results of analysis of the conjugated diene polymer thus prepared are shown in Table 2 below.

TABLE 2

|  | Initiator | Reaction time for initiator preparation | Formula 3/ lithium | Moles of lithium (mmol) | Mn (expected) | Mn | Mw | PDI |
|---|---|---|---|---|---|---|---|---|
| Example 4 | Formula 1 | 1 hr | 0.5:1 | 0.4 | 74 | 38.9 | 52.8 | 1.36 |
| Example 5 | Formula 1 | 4 hr and 30 min | 0.5:1 | 0.4 | 74 | 47.0 | 66.8 | 1.42 |
| Example 6 | Formula 1 | 25 hr | 0.5:1 | 0.4 | 74 | 48.8 | 76.2 | 1.56 |
| Example 7 | Formula 1 | 1 hr | 0.66:1 | 0.4 | 74 | 68.0 | 102.8 | 1.51 |
| Comparative Example 4 | n-BuLi | — | — | 0.4 | 37 | 37.4 | 43.2 | 1.15 |

GPC × $10^4$ (g/mol)

As can be seen from the results in Table 2 above, the molecular weights of the modified conjugated diene polymers prepared in Examples 4 to 7 of the present disclosure were higher than that of the conjugated diene polymer prepared in Comparative Example 4 using the conventional organic lithium initiator. Such results suggest that the polymerization initiators of Examples 4 to 7 functioned as a coupling agent.

Example 8

1) Preparation of 2-ethyl-6-methyl pyridine

In a 250-ml 3-neck jacketed reactor flask, 4.3 g (40.2 mmol) of 2,6-dimethylpyridine and 4.06 g (40.2 mmol) of triethylamine were dissolved by addition of 50 ml of anhydrous tetrahydrofuran, and the solution was cooled to −40° C., after which 28.7 ml (46 mmol) of 1.6 M n-butyllithium in hexane was added dropwise thereto. At the same time, the solution changed to deep red. Next, the solution was stirred for 1 hour, and then warmed to 0° C., after which 5.7 g (40.2 mmol) of methyl iodide was added dropwise thereto, followed by stirring for 1 hour. Then, the reaction product was concentrated, and the concentrate was dissolved in ethyl acetate, washed with water and saline, dried with anhydrous magnesium sulfate, and then concentrated again, thereby obtaining crude 2-ethyl-6-methylpyridine.

The obtained crude 2-ethyl-6-methylpyridine was purified by column chromatography (stationary phase: silicagel; eluent: n-hexane/ethyl acetate (6/1)), thereby obtaining 3.2 g of 2-ethyl-6-methylpyridine as liquid. The obtained 2-ethyl-6-methylpyridine was analyzed by NMR.

$^1$H NMR (CDCl$_3$, ppm): 1.24 (10H, m), 2.55 (4H, m), 2.92 (4H, q), 7.12 (4H, t), 7.66 (4H, dd)

2) Preparation of Polymerization Initiator

In a flask in a glove box purged well with argon gas, 2 mmol of N,N,N',N'-tetramethylethylenediamine and 1.14 mmol of the above-prepared 2-ethyl-6-methylpyridine were added to 150 ml of cyclohexane, and the 2 mmol of n-BuLi wad added thereto. The mixture was stirred for 16 hours, thereby preparing a polymerization initiator.

3) Preparation of Modified Conjugated Diene Polymer 20 g of isoprene was added to the prepared polymerization initiator and polymerized for 3 hours, and then 2-propanol was added thereto to stop the polymerization reaction. Then, an antioxidant was added to the polymerization product in an amount of 1 parts by weight based on 100 parts by weight of the polymerization product, and the mixture was stirred to disperse the antioxidant. The stirred mixture was precipitated, thereby obtaining a modified conjugated diene polymer. The results of analysis of the prepared modified conjugated diene polymer are shown in Table 3 below.

Example 9

1) Preparation of 2,6-diethyl pyridine

In a 250-ml 3-neck jacketed reactor flask, 4.3 g (40.2 mmol) of 2,6-dimethylpyridine and 4.06 g (40.2 mmol) of triethylamine were dissolved by addition of 50 ml of anhydrous tetrahydrofuran, and the solution was cooled to −40° C., after which 28.7 ml (46 mmol) of 1.6 M butyllithium in hexane was added dropwise thereto. At the same time, the solution changed to deep red. Next, the solution was stirred for 1 hour, and then warmed to 0° C., after which 5.7 g (40.2 mmol) of methyl iodide was added dropwise thereto, followed by stirring for 1 hour. Then, the reaction product was concentrated, and the concentrate was dissolved in ethyl acetate, washed with water and saline, dried with anhydrous magnesium sulfate, and then concentrated again, thereby obtaining crude 2-ethyl-6-methylpyridine. Subsequently, 3.2 g of the obtained 2-ethyl-6-methylpyridine was placed in a 250-ml 3-neck jacketed reactor flask and dissolved by addition of 4.06 g (40.2 mmol) of triethylamine and 50 ml of anhydrous tetrahydrofuran. The solution was cooled to −40° C., and 28.7 ml (46 mmol) of 1.6 M n-butyllithium in hexane was added dropwise. At this time, the solution changed to deep red. Next, the solution was stirred for 1 hour, and then cooled to 0° C., after which 6.0 g (42 mmol) of methyl iodide was added thereto dropwise. Then, the cooling bath was removed, and the solution was stirred at room temperature for 1 hour, and then concentrated. The concentrate was dissolved in ethyl acetate, washed with water and saline, dried with anhydrous magnesium sulfate, and then concentrated again. The concentrate was purified by column chromatography (stationary phase: silicagel; eluent: n-hexane/ethyl acetate (6/1), thereby obtaining 2 g of 2,6-diethyl pyridine as liquid. The obtained 2,6-diethyl pyridine was analyzed by NMR.

$^1$H NMR (CDCl$_3$, ppm): 1.24 (10H, m), 2.92 (4H, q), 7.14 (4H, t), 7.59 (4H, dd)

2) Preparation of Polymerization Initiator and 3) Preparation of Modified Conjugated Diene Polymer A modified conjugated diene polymer was prepared in the same manner as Example 8, except that 1.14 mmol of 2,6-diethyl pyridine was added during the preparation of the polymerization initiator. The results of analysis of the prepared modified conjugated diene polymer are shown in Table 3 below.

Example 10

A modified conjugated diene polymer was prepared in the same manner as Example 8, except that 1.14 mmol of 2,6-dimethyl pyridine was added during the preparation of the polymerization initiator. The results of analysis of the prepared modified conjugated diene polymer are shown in Table 3 below.

Comparative Example 5

A modified conjugated diene polymer was prepared in the same manner as Example 8, except that 1 mmol of n-butyllithium that is not the polymerization initiator of the present disclosure was added during the preparation of the polymerization initiator. The results of analysis of the prepared conjugated diene polymer are shown in Table 3 below.

The molecular weights of the conjugated diene copolymers prepared in the Examples of the present disclosure and in the Comparative Example were measured by gPC (gel permeation chromatography).

TABLE 3

| | Initiator | Reaction time for initiator preparation | Formula 3/ lithium | Moles of lithium (mmol) | Mn (expected) | GPC × 10$^4$(g/mol) | | |
| --- | --- | --- | --- | --- | --- | --- | --- | --- |
| | | | | | | Mn | Mw | PDI |
| Example 8 | Formula 1 | 16 hr | 0.57:1 | 2 | 2 | 38.9 | 2.4 | 1.13 |
| Example 9 | Formula 1 | 16 hr | 0.57:1 | 2 | 2 | 47.0 | 2.0 | 1.12 |
| Example 10 | Formula 1 | 16 hr | 0.57:1 | 2 | 2 | 48.8 | 1.7 | 1.30 |
| Comparative Example 5 | n-BuLi | — | — | 1 | 2 | 37.4 | 2.0 | 1.12 |

As can be seen from the results in Table 3 above, the molecular weights of the modified conjugated diene polymers prepared in Examples 8 to 10 were substantially equal to that of the conjugated diene polymer prepared in Comparative Example 5 using the conventional organic lithium initiator, even though the amount of initiator added was about two times larger than that in Comparative Example 5. This suggests that the polymerization initiator of the present disclosure also functioned as a coupling agent.

Example 11

1) Preparation of Polymerization Initiator

In a 250-ml round bottom flask, 0.33 g (0.3 mmol) of 2,6-dimethylpyridine and 1.06 g (0.9 mmol) of N,N,N',N'-tetramethylethylenediamine were dissolved by addition of 16.5 ml of hexane, and 1.52 ml (0.4 mmol) of 2.5 M n-butyl lithium was added to the solution. At this time, the solution changed to clear red. Then, the solution was stirred for 1 hour, thereby preparing a polymerization initiator.

2) Preparation of Modified Conjugated Diene Polymer 200 g of styrene, 600 g of 1,3-butadiene and 3,200 g of n-hexane were introduced into a 10-L reactor, and then heated with stirring to control the internal temperature of the reactor to 60° C. When the temperature reached 60° C., the above-prepared polymerization initiator was introduced into the reactor, and the mixture was adiabatically heated until the reaction became stable. After adiabatic heating, the reaction temperature was increased to 70° C., and after 60 minutes, the polymerization reaction was stopped by addition of methanol. Then, 5 ml of a solution of 0.3 wt % of the antioxidant BHT (butylated hydroxytoluene) in hexane was added thereto.

The polymerization product was added to steam-heated hot water, and the solvent was removed by stirring. Then, the remaining material was roll-dried to remove the remaining solvent and water. The results of analysis of the modified conjugated diene polymer thus prepared are shown in Table 4 below.

Example 12

1) Preparation of Polymerization Initiator

In a 250-ml round bottom flask, 0.25 g (0.23 mmol) of 2,6-dimethylpyridine and 0.81 g (0.7 mmol) of N,N,N',N'-tetramethylethylenediamine were dissolved by addition of 17.5 ml of hexane, and 1.2 ml (0.3 mmol based on lithium) of 2.5 M n-butyllithium was added to the solution. At this time, the solution changed to clear red. Then, the solution was stirred for 1 hour, thereby preparing a polymerization initiator.

2) Preparation of Modified Conjugated Diene Polymer

A polymerization product was obtained in the same manner as Example 11. To the polymerization product solution, aromatic oil (IDEA) was added in an amount of 37.5 parts by weight based on 100 parts by weight of the polymerization product, thereby obtaining an oil-containing polymerization or copolymerization product.

The polymerization product was added to steam-heated hot water, and the solvent was removed by stirring. Then, the remaining material was roll-dried to remove the remaining solvent and water. The results of analysis of the modified conjugated diene polymer thus prepared are shown in Table 4 below.

Comparative Example 6

A conjugated diene polymer was prepared in the same manner as Example 11, except that 0.16 ml (0.4 mmol based on lithium) of 2.5 M n-butyllithium (NBL)/hexane solution was used instead of the polymerization initiator of the present disclosure and that 1.06 g (0.9 mmol) of N,N,N',N'-tetramethylethylenediamine was used. The obtained polymerization product was treated in the same manner as Example 11. The results of analysis of the conjugated diene polymer thus prepared are shown in Table 4 below.

Comparative Example 7

A conjugated diene polymer was prepared in the same manner as Example 12, except that 1.2 ml (0.3 mmol based on lithium) of 2.5 M n-butyllithium (NBL)/hexane solution was used instead of the polymerization initiator of the present disclosure and that 0.81 g (0.7 mmol) of N,N,N',N'-tetramethylethylenediamine was used. The obtained polymerization product was treated in the same manner as Example 12. The results of analysis of the conjugated diene polymer thus prepared are shown in Table 4 below.

TABLE 4

| | | Example 11 | Example 12 | Comparative Example 6 | Comparative Example 7 |
|---|---|---|---|---|---|
| Sample | | A | B | C | D |
| Initiation time | | Formula 1 | Formula 1 | n-BuLi | n-BuLi |
| Modification time | | 1 hr | 1 hr | — | — |
| TDAE oil | | — | 37.5 phr | — | 37.5 phr |
| MV | | 48.8 | 35.2 | 55.7 | 41.3 |
| −S/R | | 1.019 | 1.221 | 0.855 | 1.883 |
| DSC (° C.) | Tg | −27.68 | −33.08 | −29.56 | −32.23 |
| NMR (%) | SM | 25 | 25 | 25 | 25 |
| | Vinyl | 40 | 41 | 40 | 42 |
| GPC (×10$^4$) | Mn | 26.0 | 33.1 | 27.9 | 34.2 |
| | Mw | 32.5 | 47.0 | 31.2 | 42.2 |
| | PDI | 1.25 | 1.42 | 1.12 | 1.23 |

Each of the samples (A to D) shown in Table 4 above was used as a raw material rubber and blended under the conditions shown in Table 5 below, thereby preparing conjugated diene polymer rubber compositions. Samples A and C were blended under the blending condition of S-1, and samples B and D were blended under the blending condition of S-2.

With respect to the kneading of the conjugated diene polymer compositions, in stage-1 kneading, the raw material rubber (conjugated diene polymer), a filler, an organosilane coupling agent, oil, zinc oxide, a stearic acid antioxidant, an anti-aging agent, wax and an accelerator were kneaded at 80 rpm using a Banbury mixer equipped with a temperature controller. The temperature of the kneader was controlled, and a first blend was obtained at a discharge temperature of 140 to 150° C. In stage-2 kneading, the first blend was cooled to room temperature, and then rubber, sulfur and a vulcanization accelerator were added to the kneader, and a second blend was obtained at a discharge temperature of 45 to 60° C. In stage-3 kneading, the second blend was molded and vulcanized with a vulcanization press at 180° C. for T90+10 minutes, thereby preparing vulcanized rubbers.

The physical properties of each of the prepared vulcanized rubbers were measured according to the following methods.

1) Tensile Test

According to the tensile test method of ASTM 412, the tensile strength at break and the tensile stress at 300% elongation (300% modulus) were measured.

2) Viscoelastic Property

A dynamic mechanical analyzer (TA Instruments, Inc.) was used. The Tan δ was measured at varying temperatures (0-60° C.) in a twist mode at a frequency of 10 Hz while changing strain. The Payne effect was expressed as a difference between the highest value and the lowest value at a strain of 0.2-40%. The smaller the Payne effect, the better the dispersibility of a filler such as silica. The higher the Tan δ at 0° C., the better the wet skid resistance. In addition, the higher the Tan δ at 60° C., the lower the hysteresis loss, and the lower the rolling resistance (i.e., high fuel efficiency). The properties of the vulcanized rubbers are shown in Table 6 below.

TABLE 5

|  | S-1 (parts by weight) | S-2 (parts by weight) |
| --- | --- | --- |
| Rubber | 100.0 | 137.5 |
| Silica | 70.0 | 70.0 |
| Coupling agent | 11.2 | 11.2 |
| Oil | 33.75 |  |
| Zinc oxide | 3.0 | 3.0 |
| Stearic acid | 2.0 | 2.0 |
| Antioxidant | 2.0 | 2.0 |
| Anti-aging agent | 2.0 | 2.0 |
| Wax | 1.0 | 1.0 |
| Rubber accelerator | 1.75 | 1.75 |
| Sulfur | 1.5 | 1.5 |
| Vulcanization accelerator | 2.0 | 2.0 |
| Total parts by weight | 230.2 | 234.0 |

TABLE 6

|  | Comparative Example 8 | Example 13 | Comparative Example 9 | Example 14 |
| --- | --- | --- | --- | --- |
| Copolymer | C | A | D | B |
| Mooney viscosity of blend | 42.3 | 39.0 | 55.5 | 54.7 |
| 300% modulus (Kgf/cm$^2$) | 111 | 125 | 102 | 117 |
| Tensile strength (Kgf/cm$^2$) | 179 | 183 | 178 | 172 |
| Tanδ at 0° C. | 0.549 | 0.703 | 0.519 | 0.628 |
| Tanδ at 60° C. | 0.090 | 0.087 | 0.083 | 0.074 |
| 60° C. Δg' (Payne effect) | 0.43 | 0.37 | 0.43 | 0.38 |

As can be seen from the results in Table 6 above, in the case of the modified conjugated diene polymer compositions of Examples 13 and 14 according to the present disclosure, the 300% modulus was greatly increased, and the Tan δ at 0° C. was higher than that in the case of Comparative Examples 8 and 9. Thus, it is obviously expected that a tire comprising the modified conjugated diene polymer rubber composition of the present disclosure will have high wet skid resistance.

In addition, in the case of the modified conjugated diene polymer compositions of Examples 13 and 14 according to the present disclosure, the Tan δ at 60° C. was lower than that in the case of Comparative Examples 8 and 9. Thus, it is obviously expected that a tire comprising the modified conjugated diene polymer rubber composition of the present disclosure will have rolling resistance lower than that of the prior art. This demonstrates that the Payne effect was lower in Examples 13 and 14 than Comparative Examples 8 and 9, suggesting that silica was more sufficiently dispersed in the case of Examples 13 and 14. Such changes in the physical properties are attributable to a significant improvement in dispersion of silica caused by the use of the modified conjugated diene polymer of the present disclosure.

As described above, the present disclosure provides a modified conjugated diene polymer, which has a high vinyl content, excellent compatibility with inorganic fillers and good properties in terms of braking force, viscoelasticity, wear performance and fuel economy, and a tire comprising the modified conjugated diene polymer and having low rolling resistance and excellent wet skin resistance.

What is claimed is:

1. A polymerization initiator which is a compound represented by Formula 1:

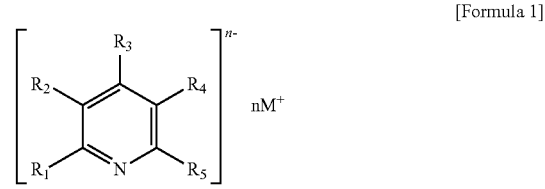

[Formula 1]

wherein $R_1$ is carbanion of a $C_{1-10}$ alkyl group; $R_2$ to $R_5$ are hydrogen; n– represents the number of negative charges of the carbanion and is 1– to 5–; M is a metal;

wherein the polymerization initiator is made by reacting a compound represented by Formula 3 with a compound represented by Formula 4:

[Formula 3]

wherein $R_6$ is a $C_{1-10}$ alkyl group; and $R_7$ to $R_{10}$ are hydrogen; and

$R(Li)_x$ [Formula 4]

wherein R is a $C_{1-20}$ hydrocarbyl group, and x is an integer ranging from 1 to 4, wherein a molar ratio between the compound of Formula 3 and the compound of Formula 4 is 1:1.1 to 1:1.4.

2. The polymerization initiator of claim 1, wherein n is 1 or 2.

3. The polymerization initiator of claim 1, wherein M is an alkali metal.

4. A polymerization initiator solution comprising a polymerization initiator represented by Formula 1, a solvent and a polar additive:

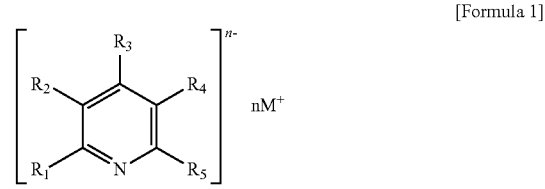

[Formula 1]

wherein $R_1$ is carbanion of a $C_{1-10}$ alkyl group; $R_2$ to $R_5$ are hydrogen; n– represents the number of negative charges of the carbanion and is 1– to 5–; M is a metal;

wherein the polymerization initiator is made by reacting a compound represented by Formula 3 with a compound represented by Formula 4:

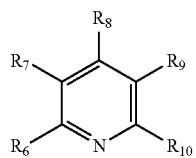

[Formula 3]

wherein $R_6$ is a $C_{1-10}$ alkyl group; and $R_7$ to $R_{10}$ are hydrogen; and $$R(Li)_x \qquad \text{[Formula 4]}$$

wherein R is a $C_{1-20}$ hydrocarbyl group, and x is an integer ranging from 1 to 4, wherein a molar ratio between the compound of Formula 3 and the compound of Formula 4 is 1:1.1 to 1:1.4.

5. The polymerization initiator solution of claim 4, wherein the polar additive is contained in an amount of 0.1-40 moles per mole of the compounds represented by formula 1.

6. The polymerization initiator solution of claim 4, wherein the polar additive is a base.

7. The polymerization initiator solution of claim 4, wherein the polar additive is ether, amine or a mixture thereof.

8. The polymerization initiator solution of claim 4, wherein the polymerization initiator solution is used for preparation of a conjugated diene polymer.

\* \* \* \* \*